United States Patent
Rapin et al.

(10) Patent No.: US 7,265,156 B2
(45) Date of Patent: Sep. 4, 2007

(54) MEDICINAL ASSOCIATION OF A BIGUANINE AND A CARRIER, FOR EXAMPLE METFORMIN AND ARGININE

(75) Inventors: Jean-Robert Rapin, Paris (FR); Dominique Halbitte, Lyons (FR)

(73) Assignee: Dospharma, Mont St Aignan (FR)

( * ) Notice: Subject to any disclaimer, the term of this patent is extended or adjusted under 35 U.S.C. 154(b) by 432 days.

(21) Appl. No.: 10/465,997

(22) PCT Filed: Dec. 31, 2001

(86) PCT No.: PCT/FR01/04235

§ 371 (c)(1), (2), (4) Date: Oct. 3, 2003

(87) PCT Pub. No.: WO02/053090

PCT Pub. Date: Jul. 11, 2002

(65) Prior Publication Data
US 2004/0097399 A1    May 20, 2004

(30) Foreign Application Priority Data
Dec. 29, 2000 (FR) .................................. 00 17332

(51) Int. Cl.
*A01N 37/52* (2006.01)
*A61K 31/155* (2006.01)
(52) U.S. Cl. ..................... 514/635; 564/233
(58) Field of Classification Search .................. 514/635
See application file for complete search history.

(56) References Cited

U.S. PATENT DOCUMENTS 6,031,004 A * 2/2000 Timmins et al. ............. 514/635
6,475,521 B1 * 11/2002 Timmins et al. ............. 424/469

FOREIGN PATENT DOCUMENTS

| FR | 2 037 002 A | 12/1970 |
| FR | 2 696 740 A1 | 4/1994 |
| FR | 2 796 551 A1 | 1/2001 |
| WO | WO99 29314 A1 | 6/1999 |
| WO | WO99 55320 A1 | 11/1999 |
| WO | WO 02 12177 A1 | 2/2002 |

OTHER PUBLICATIONS

R. Marfella et al., "Metformin improves hemodynamic and rheological responses to L-arginine in NIDDM patients," *Diabetes Care*, vol. 19, No. 9, pp. 934-939, Sep. 1996.

* cited by examiner

Primary Examiner—Sreeni Padmanabhan
Assistant Examiner—Umamaheswari Ramachandran
(74) Attorney, Agent, or Firm—Oliff & Berridge, PLC

(57) ABSTRACT

The present invention relates to a compound of formula III,

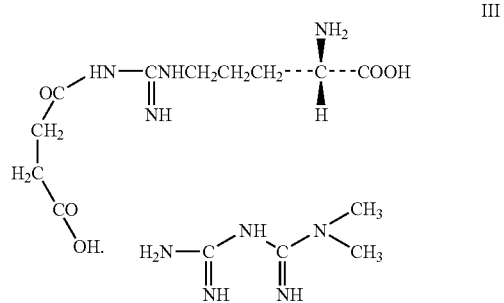

method of making the same and its use in the treatment of diabetes.

3 Claims, 1 Drawing Sheet

FIGURES

*FORMULA I: ARGININE*

I

*FORMULA II: METFORMIN*

II

*FORMULA III: ARGININE HEMISUCCINIMIDE-METFORMIN HEMI-SUCCINATE*

III

MEDICINAL ASSOCIATION OF A BIGUANINE AND A CARRIER, FOR EXAMPLE METFORMIN AND ARGININE

FIELD OF THE INVENTION

The present invention relates to a medicinal combination of two active principles, having, jointly, a complementary and/or synergistic action, this being for the treatment of diabetes, in particular of type 2 diabetes.

The expression "complementary action" is intended to mean the pharmacological action of two different compounds making it possible to act on the same pathology via two respectively different pharmacological mechanisms, for example the combined use of two anti diabetic agents, such as a biguanide and a sulfonylurea.

The expression "synergistic actions" is intended to mean the pharmacological action of two compounds, consisting in potentiating the action of at least one of said compounds, for example potentiation of the action of a biguanide by the action of a transporter as described and proposed hereinafter in the invention.

BACKGROUND OF THE INVENTION

It is known that metformin in the form of hydrochloride is the first choice medicine in the treatment of hyperglycemia and of non-insulin dependent diabetes. This metformin hydrochloride is used alone or in combination with a sulfonylurea, an alpha-amylase inhibitor or a glitazone.

Metformin hydrochloride at the dose of 50 mg/kg in rats is active on conventional models of non-insulin dependent diabetes such as the streptozotocine model and the fructose model.

It has low bioavailability (60%) and its entry through the intestine occurs preferentially in the jejunum and in the ileum. This low bioavailability explains the bothersome side effect of metformin, namely diarrhea.

Metformin is a very basic biguanide which is completely ionized at intestinal pH values. Its entry therefore involves a physiological transporter system, which explains the preferential entry.

SUMMARY OF THE INVENTION

An object of the present invention is to reduce the side effects and to improve the bioavailability of the metformin by acting on this physiological transporter system.

Surprisingly, the present invention has demonstrated that, when associated with metformin, an amine or polyamine, having structural similarity with a biguanide, and, in particular with an N-dimethylbiguanide, has indeed this role of transporter with respect to the metformin. More particularly, among transporters, arginine is preferred because of the similarity of its chemical structure with metformin. Specifically, L-arginine (see FIG. 3) activates itself its own intestinal transfer. In addition, arginine is the precursor for the synthesis of the nitroso radical NO, which is recognized as being one of the most potent vasodilators, both of veins and of arteries, and for its hemodynamic and hemorheological properties. This action characteristic of arginine might be beneficial for pathologies secondary to the development of diabetes, namely macroangiopathies, microangiopathies, neuropathies, nephropathies and retinitis of diabetics.

In accordance with the document "Marfella R. et al., Metformin improves hemodynamic and Theological responses to L-arginine in NIDDM patients, Diabetes care, 1996 sep 19(9) 934-9", an experiment is described in humans, outside any clinical or therapeutic protocol, consisting in administering by the intravenous route (under infusion) a total dose of 30 g of arginine over 30 min, which is enormous and unachievable in common therapy.

In accordance with this same document, it has been shown that the simultaneous administration of metformin potentiates the hemodynamic and hemorheological action of aginine. However, by contrast, the therapeutic effects specific to metformin, in particular the antihyperglycemic effects, are not modified by arginine.

Thus, the results obtained according to the invention, on experimental models of diabetes, have shown that metformin active compounds having, within their structure, an arginine residue, were capable of increasing the bioavailability of the metformin, in an unexpected manner, by potentiating its effects against hyperglycemia, which is the main symptom of diabetes.

All the biguanides currently used, or being developed, in the treatment of diabetes have the side effects and the problems of bioavailability cited above.

Among the amines or polyamines which have a structural similarity with biguanides, and which can be combined as a transporter with these biguanides, those which are natural for the human physiology, i.e. biogenic, and/or those which are pharmacologically and therapeutically active, are preferred.

Among the pharmacologically and therapeutically active amines or polyamines, those belonging to the same therapeutic class as metformin, or those making it possible to act on a pathology which is associated with diabetes are preferred.

Among the amines or polyamines which are natural for human physiology, i.e. biogenic, those which are metabolizable, biodegradable by integration into an endogenous metabolic cycle, into conventional metabolites will be preferred.

The present invention relates to a medicinal set for the treatment of diabetes, in particular of type 2 diabetes, combining a biguanide, in particular an N-dimethylbiguanide, as a first medicament, and an agent for transporting the said biguanide, as a second medicament, said set comprising:

a) a therapeutically active quantity of the biguanide
b) and a quantity of transporting agent, previously determined to potentiate the therapeutic activity of the biguanide according to (a).

It also relates to a set as described above, characterized in that the biguanide according to (a) and the transporting agent according to (b) are in an equimolar quantity.

It also relates to a set as described above, characterized in that the biguanide is metformin.

It also relates to a set as defined above, characterized in that the transporting agent is a biogenic amine, for example chosen from the group consisting of arginine, putrescine, cadaverine, spermidine, spermine, and is for example L-arginine.

It also relates to a set as described above, characterized in that the biguanide and/or the transporting agent are in a form suitable for their controlled release respectively, The set according to the invention, chemically put together for the controlled release of at least biguanide, is also characterized in that it is an active compound of general formula A'-----V'-----C', capable of restoring at least the entity A by cleavage, in vivo, of the corresponding attachment between A' and V', it being specified that:

V is a biogenic vectorization compound, of general formula X—R—Y, in which,

R represents an aliphatic, cyclic or alicyclic, saturated or unsaturated hydrocarbon chain of 2 to 10 carbon atoms, which is optionally substituted with C1 to C5 alkyl groups and/or hydroxyl groups, X and Y are each a free acid, amine or alcohol function.

A and C are two respectively different active principles, namely the biguanide and the transporter, one of which comprises a chemical function complementary to the function X, capable of reacting with the latter so as to give an ionic A' - - - V' or covalent A'-V' attachment which can be cleaved in vivo, and the other of which comprises a chemical function complementary to the function Y, capable of reacting with the latter so as to give an ionic V' - - - C' or covalent V'-C' attachment which can be cleaved in vivo.

The set defined above is in a variant according to the invention, characterized in that, the V' - - - C' or V'-C' attachment can be cleaved in vivo, and said active compound is also capable of restoring the entities V and C by said cleavage in vivo.

The invention also relates to an active compound as defined above, A being metformin, characterized in that the metformin is attached to the biogenic vectorization compound by salification of the terminal primaine [sic] amine function of the metformin.

The invention also relates to an active compound as defined above, characterized in that when C is arginine, the arginine is attached to the biogenic vectorization compound V using an acylation reaction.

The invention also relates to an active compound as defined above, characterized in that V is chosen from among the set of diacids consisting of oxalic, malonic, succinic, glutaric, adipic, pimelic, suberic, azelaic, sebactic [sic], malic, isatic and phthalic acids, and preferably succinic acid.

The invention also relates to an active compound of formula III

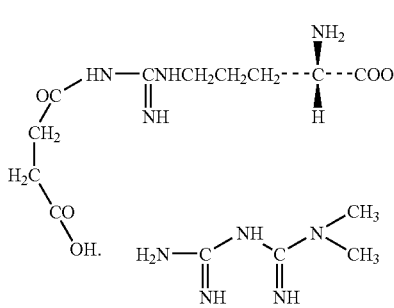

The invention also relates to the use, as medicine, of a compound as defined above.

It relates, more particularly, to the use, as medicine, of a compound of general formula A'-----V'-----C' as defined above.

The invention also relates to a process for preparing an active compound according to the invention, comprising the following steps:

a) reaction for condensation and/or salification of the biogenic vectorization compound V with one of the active principles A or C, b) reaction for condensation and/or salification of the product of the reaction according to (a) with the other active principle C or A.

Another subject of the invention is a pharmaceutical composition comprising at least one compound according to the invention, in combination with one or more compatible and pharmaceutically acceptable vehicles, diluents, excipients or adjuvants.

Another subject of the invention is also the pharmaceutical composition as defined above, which makes it possible to adjust a daily dose in humans of between approximately 0.2 g and approximately 1 g of the said active compound, to one or more doses.

In the antidiabetic or antihyperglycemic indication, a medicinal set (or therapeutic treatments kit) according to the invention, and in particular an active compound of formula A'-----V'-----C' as defined above, may be combined with another antihyperglycemic agent such as a sulfonylurea.

DETAILED DESCRIPTION OF THE INVENTION

Figure 1:
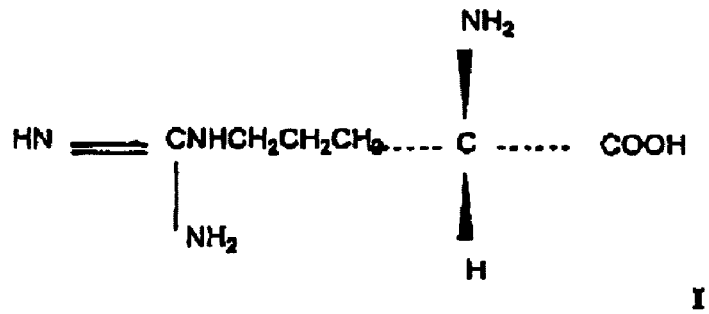
FIGS. 1-3 show exemplary formulae for the arginine, the metformin and the salt of the arginine hemisuccinimide with the metformin, respectively.

The expression "biguanide" is understood to mean in particular N-dimethylbiguanides, substituted or otherwise, and for example metformin, but also other pharmaceutical compounds, for example buformin or fenformin.

Preferably, the biguanide is metformin.

The expression "simultaneous administration" is intended to mean the administration, in a single dose, of the two active principles, it being understood that the simultaneous administration allows the release, in the organism, of the two active principles simultaneously or in sequence.

The term "biogenic" is intended to mean a chemical compound which is of natural or unnatural origin and/or is metabolizable and/or is biodegradable and/or is atoxic with respect to the human or the animal, at a physiological dose.

The term "transporter" is intended to mean a molecule or substance which allows the transfer of another molecule across a barrier, either by forming an attachment, or without forming an attachment, by activating the transport system, for example by protein induction, activation of oxygen-dependent ATPase systems or by substance exchange.

More particularly, the term "transporter" is intended to mean herein any molecule or substance making it possible to potentiate the entry of a biguanide such as metformin, and therefore to facilitate the transport thereof in the jejunum.

For the implementation of a medicinal combination as defined above, various administration solutions can be considered, such as for example:

a pharmaceutical formulation or presentation making it possible to administer, in a single dose, both the biguanide and the transporter or two respectively different pharmaceutical presentations making it possible, in a suitable packaging, to administer, at the same time and respectively, both a dose of biguanide and a dose of transporter.

Quite particularly, and preferably, this implementation is carried out using an active compound of general formula A'-----V'-----C', capable of restoring the entities A, V and C by cleavage, in vivo, of the corresponding attachments between A', V' and C', it being specified that:

V is a biogenic vectorization compound, of general formula X—R—Y, in which,

R represents an aliphatic, cyclic or alicyclic, saturated or unsaturated hydrocarbon chain of 2 to 10 carbon atoms, which is optionally substituted with C1 to C5 alkyl groups and/or hydroxyl groups, X and Y are each a free acid, amine or alcohol function.

A and C are two respectively different active principles, namely the biguanide and the transporter, one of which comprises a chemical function complementary to the function X, capable of reacting with the latter so as to give an ionic A' - - - V' or covalent A'-V' attachment which can be cleaved in vivo, and the other of which comprises a chemical function complementary to the function Y, capable of reacting with the latter so as to give an ionic V' - - - C' or covalent V'-C' attachment which can be cleaved in vivo.

The expression "cleavage in vivo" is intended to mean herein all forms of chemical hydrolysis, likely to be observed in vivo, for example, acid hydrolysis and enzymatic hydrolyses by amidases or esterases, for example.

The expression "complementary chemical function" is intended to mean any chemical function capable of reacting with a free or terminal function of the biogenic compound. For example, V has to comprise a function which reacts with A (biguanide) and a function which reacts with C (transporter). Thus, if A and C each have an acid function, V is a diamine, a dialcohol or an alcohol-amine, so as to form, respectively, an amide, an ester or a salt. Thus, if A and C each have an amine function, V is a diacid so as to form an amide or a salt. If A and C each have an alcohol function, V is a diacid so as to form a diester. With this principle, all compositions are possible. Consequently, if A has an acid function and C an alcohol function, V is, for example, an alcohol-amine, so as to act with the acid function of A to give an amide, an ester or a salt, and with the alcohol function of C to give an ester.

The expression "covalent attachments" is herein intended to mean chemical attachments capable of being formed, by reaction of so-called complementary chemical functions, between the biogenic vectorization compound V and the active principles A (biguanide) And C (transporter).

The expression "ionic attachments" is herein intended to mean attachments via electrostatic force, capable of being formed, by action of the so-called complementary chemical functions, between the biogenic vectorization compound V and the active principles A (biguanide) and C (transporter), therefore attachments of the acid salt, amine salt, alkoxide and acid/base type, and this being independently of the molar proportion existing between the compound V and the active principle A or C, belonging to the complex formed by said ionic attachments.

The expression "attachment which can be cleaved in vivo" is intended to mean any attachment which allows the release or restoration of the active principles A (biguanide) and C (transporter), and of the biogenic vectorization compound V, in vivo, by breaking the ionic or covalent attachments between the complementary chemical functions of A and V, and of C and V.

The covalent attachments which can be cleaved are cleaved by the action of the enzymes present in the in vivo medium of the site of release. Since these covalent attachments are amide attachments or ester attachments, the enzymes involved in this cleavage are amidases, esterases and hydrolases. These enzymes are present in particular in the digestive tract (oral administration), predominantly in the liver and in the bloods and are potentially present in the target organs.

Amidases which hydrolyse the attachment —CO—NH— are found in the liver, they are relatively inactive; hence an expected sustained effect with the compound according to the invention bearing such an attachment. Among these amidases, some are known; they are endopeptidases which hydrolyse gamma-amine-containing or gamma acid attachments. According to the invention, V can in fact be a gamma-amino acid, with a second acid or amine function in the gamma position (in the case of glutamic acid or of lysine, for example).

Esterases which hydrolyse the attachment —CO—O— are extremely numerous in living organisms. They are, however, ubiquitous and relatively non-specific for a substrate, hence a high reaction rate, with rapid release of the constituents A (biguanide), V, C (transporter) of the active compound according to the present invention. Those most specific for a substrate bear the name of this substrate and, by way of this, mention may be made, for example, of cholinesterases or procaine esterases.

Hydrolases also hydrolyse esters and all large molecules supplied to the organism in the form of foods. These hydrolases are numerous and ubiquitous also. They will, however, be specific for the biogenic vectorization compound V used.

As cleavage enzymes which can be used for implementing the present invention, mention may be made of proteolytic enzymes such as pepsin, trypsin, catalases, and endo- and exopeptidases. Enzymes which can also be used are amylases and osidases, and finally lipases and beta-oxygenases for the destruction of lipids.

These enzymes are involved only when the structure of the biogenic vectorization compound comprises one or more attachments which they are capable of cleaving. For example, the lipase acts if the biogenic vectorization compound is a long chain diacid (8 to 10 carbon atoms, comparing it to a fatty acid), and the A-V or V-C attachment is obtained by condensation with a secondary alcohol function of A or of C.

The ionic attachments which can be cleaved are cleaved as a function of their site of release, for example intestine, liver, plasma or target organ, it being understood that acid salts or amine salts or alkoxides are generally ionized at the pH is of the media of living organisms. Generally, the pH is between 2 and 8 and is, for example, 2 for the stomach and 6, for example, for the intestine.

There is therefore ionization of the active compound according to the invention, as a function of the type of salt used, and a dissociation of said active compound, when the latter comprises at least one ionic attachment. The salt is chosen as a function of its dissociation constant and of the pH of the in vivo site of release. For example, for dissociation in the stomach, a salt of a weak acid and of a strong base is chosen.

The choice of the biogenic vectorization compound, and in particular the choice of its free functions X and Y, is made according to the nature of the free and complementary chemical functions present in or on the active principles (biguanide and transporter) intended to be vectorized, i.e. attached by covalent or ionic attachment to this biogenic vectorization compound, but also according to the sites of cleavage and release chosen. This biogenic vectorization compound is a product which is of natural or unnatural origin and/or is metabolizable and/or is biodegradable and/or is atoxic with respect to the human or to the animal, at a physiological dose. This biogenic vectorization compound will be chosen from biologically tested and described compounds, such as gamma-amino acids involved in protein synthesis, biacids involved in the Kreps [sic] cycle and ethanolamines constituting cell membranes, which are metabolizable and atoxic, and capable of being integrat d, themselves or their metabolites, into the major biological cycles of life. By way of a biogenic vectorization compound, mention may be made, for example, of succinic acid which is found in the Kreps [sic] cycle or methyl succinic acid which is biodegraded to succinic acid.

The attachments selected, between the biogenic vectorization compound and the combined active principles according to the present invention, that is to say, biguanide and transporter, depend on the possible metabolisms at the gastrointestinal and hepatic level.

For example, the salts can be dissociated in the digestive tract, the hydrolysis possibly being delayed using gastro-resistant pharmaceutical forms. The esters are hydrolysed in acid medium, or hydrolysed by the esterases of the gastric juices, the hydrolysis also possibly being delayed using gastro-resistant pharmaceutical forms. The amides are hydrolysed by the hepatic amidases, the kinetics of these hydrolyses being generally slow.

Various assays can be carried out in order to evaluate the ability of the A'-----V' and V'-----C' attachments to be cleaved in vivo and of the active principles A (biguanide) and C (transporter) to be correspondingly released. These assays consist, for example, in observing the release of the active principles in an intestinal juice, or studying the hepatic metabolism on rat hepatocyte primary cultures. These two tests are described below.

In vitro Assay of Cleavage in an Intestinal Juice

A preparation of intestinal juice containing trypsin, peptidases, lipase, amylase and all the other enzymes of the exocrine pancreas is used. This assay is validated beforehand using calibration compounds. A known amount (of the order of one microgram) of the compound A'V'C' is mixed together with a known amount of intestinal juice (the trypsin and lipase contents of which are controlled). The reaction mixture is kept at 37° C. for one hour. This time is compatible with the intestinal transit. Samples are taken every 15 min, and the products A and C are detected and their concentration measured using HPLC coupled to a UV detector, or a mass spectrometer if it is not possible to use UV. The columns used depend on the nature of A and of C, but are generally ion-exchange columns, because of the presence of released alcohol, amine or acid forms. After calibration, the total amount of A (biguanide) or of C (transporter) released in 1 hour is determined, and the intermediate points make it possible to calculate the dissociation constants Km and the rate Vmax of the enzymes for the active compound A'V'C' used. This assay can be coupled with determination of the release of A (biguanide), C (transporter) and V in the gastric juice, using exactly the same principle but replacing the intestinal juice with gastric juice.

In vitro Assay on Rat Hepatocyte Primary Cultures

A primary culture of rat hepatocytes, which are close to those of humans for metabolism studies, is used, in a HEPES medium to which a known amount of compound A'V'C', of the order of one microgram, is added. The products are left in contact for 6 hours, and samples are taken, at 1 hour, 2 hours and 4 hours, on which the supernatant is isolated and the hepatocytes in the pellet are lysed. In these media, the concentrations of active principles A (biguanide) and C (transporter) released are measured. As previously, it is possible to calculate the Vmax and Km of the enzymes involved in the metabolism.

When the compounds according to the invention do not cross the cell membranes, the same type of study can be carried out on a rat liver homogenate.

The possible toxicity of the biogenic vectorization compound is related to that of the active compound (A'V'C') according to the invention. As this active compound is metabolized to A (biguanide), C (transporter) and V, and V is a substance which is by definition biological, the toxicity of the compound according to the invention must compare to the sum of the toxicities due to the administration of the biguanide A and of the transporter C. In addition, when the active compound combines two active principles having, under these conditions, at least for one active principle, an efficacy greater than that of said same active principle alone, said compound can be considered to be less toxic. However, a method for predicting the toxicity, alternative to the standard in vivo methods, is proposed hereinafter for comparing the toxicity of A and of C and of A'-----V'-----C' at identical concentrations expressed as A or as C (see Toxicologic Emergencies, Sixth Edition 1997, Goldfranck et al. Appleton and Lange, Conn., USA).

In Vitro Toxicity Assay

A method for culturing primary hepatocytes over a 96-hour period is used (see Biochemical Pharmacology, Vol. 50, 1995, pp 775-780). The hepatocytes are isolated in situ by collagenase perfusion. They are then placed in a Williams medium supplemented with foetal calf serum, with cortisol and with glutamine, in a proportion of 1 million cells per well. Increasing and toxic concentrations of A (biguanide) and C (transporter) and of A'-----V'-----C' are added to each well. Samples are taken after 6 h, 12 h, 24 h, 48 h and 96 h, and, the viability of the cells is determined with a methylene blue test, by albumin expression, by hepatocyte apoptosis and by measuring cytochrome P450 activity.

The viability of the cells with the methylene blue test gives results similar to those obtained with an $LD_{50}$.

The results obtained with the albumin expression make it possible to learn the limits of tolerance of the hepatocyte to any toxic substance (end toxicity). Specifically, one of the main roles of the hepatocyte is to synthesize proteins. During a toxic effect, this expression of albumin synthesis and release is modified.

The results obtained with hepatocyte apoptosis make it possible to confirm the end toxicity, since during a contact with a toxic substance, the cells will program their destruction, which corresponds to the phenomenon of apoptosis which is measured by the abnormal DNA.

The measurement of cytochrome P450 activity documents the phenomena of induction and of inhibition of these enzymes, often encountered with pharmacologically active products. A series of assays makes it possible to determine the activity of the cytochrome P450 isoforms.

The present invention also relates to the following variants:

A is metformin in the abovementioned general formula, the metformin is attached to the biogenic vectorization V compound by salification of the terminal primary amine function of the metformin C is arginine in the abovementioned general formula, the arginine is attached to the biogenic vectorization compound V using an acylation reaction V, in the abovementioned general formula, is chosen from the set of diacids consisting of oxalic, malonic, succinic, glutaric, adipic, pimelic, suberic, azelaic, sebactic [sic], malic, isatic and phthalic acids, and preferably succinic acid The invention also relates, as medicine, to the compound of formula III.

The invention also relates to any pharmaceutical composition comprising an active compound as defined above, in combination with one or more compatible and pharmaceutically acceptable vehicles, diluents, excipients, or adjuvants. Preferably, such a pharmaceutical composition makes it possible to adjust a daily dose in humans of between 0.2 g and 1 g of each active principle (biguanide or transporter), to one or more doses. For example, gastro-resistant pharmaceutical forms can be used in order to avoid any hydrolysis in the stomach.

Preferably, an active compound as defined above can be obtained at the end of the following steps;

reaction for condensation and/or salification of the biogenic vectorization compound (V) with one (A or C) of the active principles, reaction for condensation and/or salification of said condensed and/or salified biogenic compound obtained with the other active principle (C or A).

Conventionally, the condensation reactions which can be used are amine acylation reactions and alcohol esterification reactions.

When one (A or C) at least of the active principles (biguanide or transporter) is attached to the biogenic vectorization compound V using a salification reaction, the sequence for carrying out the reactions will preferably comprise the condensation reaction and then the salification reaction, for reasons of stability of the salts as a function of the pH, well known to those skilled in the art.

When A is metformin, C is arginine and V is succinic acid, the preparation method comprises the following steps:

reaction of the monochloride monoester of the succinic acid in solution in ether or in benzene, with the arginine in aqueous solution in sodium carbonate, release of the metformin base from the hydrochloride in concentrated sodium hydroxide medium and extraction with absolute alcohol, formation of the salt of arginine hemisuccinimide with metformin.

Preferably, the pharmaceutical compositions according to the invention are adapted in a form which is suitable for oral, parenteral or intravenous administration.

A subject of the invention is more particularly the use of at least one active compound as described above, for producing medicines intended for the treatment of diabetes in all its forms and/or for the treatment of diseases of the circulatory system, whether or not these diseases are attached to diabetes.

The present invention is now described byway of example, with reference to the combination of metformin (biguanide) and arginine (transporter) in a same active compound A'V'C', V being succinic acid reacting, on the one hand, covalently with an amine function of arginine and, on the other hand, ironically (salification [sic] reaction) with an amine function of metformin Synthesis of Arginine Hemisuccinimide Metformin Hemisuccinate a) First step: preparation of the arginine hemisuccinimide.

Arginine base (6 g) is dissolved in 120 ml of an aqueous solution of sodium carbonate (N=10.6 g/100 ml). Moreover, succinic monochloride monoester is diluted in 50 ml of sulfuric ether, with a slight excess of succinic monochloride monoester for a reaction which is mole for mole with respect to the arginine. The ether-containing solution is added to the aqueous solution in 10 minutes, with vigorous stirring at room temperature. The reaction liquid is maintained with vigorous stirring for one hour, while slowly heating for complete distillation of the ether. The mixture is evaporated to dryness, and the residue is taken up with a minimum volume of distilled water (20 ml) and acidified with diluted hydrochloric acid. By concentrating (slight heating under partial vacuum) white crystals of arginine hemisuccinimide are obtained.

The NMR spectrum, the centesimal analysis and the purity of the product by thin-layer chromatography are verified. In particular, the presence of the arginine amino acid residue is verified by the ninhydrin reaction and the presence of the free carboxyl of the succinic acid is verified by titrimetry.

The yield is quantitative.

b) Second step: release of the metformin base.

10 grams of metformin hydrochloride are added to 40 ml of a 5N sodium hydroxide solution. The reaction mixture is heated for two hours at 40° C. After evaporation under vacuum at 40° C., the viscous residue is taken up with 100 ml of absolute ethanol. Filtration allows the impurities to be eliminated and an insoluble residue of sodium chloride remains. The metformin base is in alcoholic solution and it is isolated, by evaporation, in the form of a viscous powder. The NMR spectrum confirms the structure of the metformin. The absence of chloride is verified with silver nitrate.

It is recalled that metformin, i.e. N,N-dimethylimidodicarbonimidic diamide is identified in the MERCK Index under the number 5792 and characterized under the Chemical Abstracts number 657-24-9.

c) Third step

The metformin base is added, mole for mole, to an aqueous solution of arginine hemisuccinimide. Immediate dissolving is obtained.

The water is completely evaporated off at 60° C. under vacuum. The residue is redissolved in distilled water and crystallizes during concentration under vacuum.

Translucent crystals which are soluble in water and insoluble in organic solvents are obtained. The melting point is 188-189° C.

The NMR spectrum, the centesimal analysis and the presence of a single spot after thin-layer chromatography confirm the structure and purity of the product. The total yield is quantitative.

After the above reactions, the yield is close to 90%. The losses originate from the purifications and filtrations.

Figure 2:
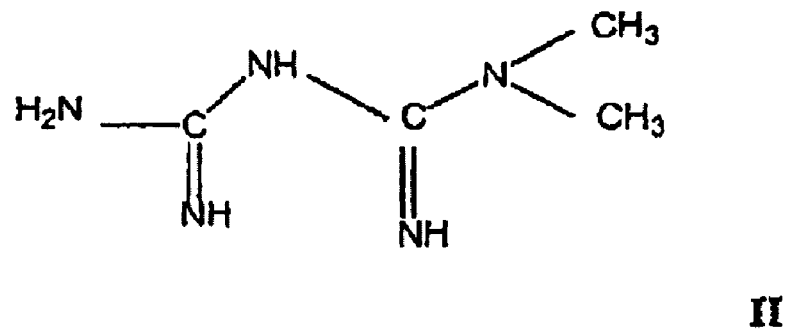
Figure 3:
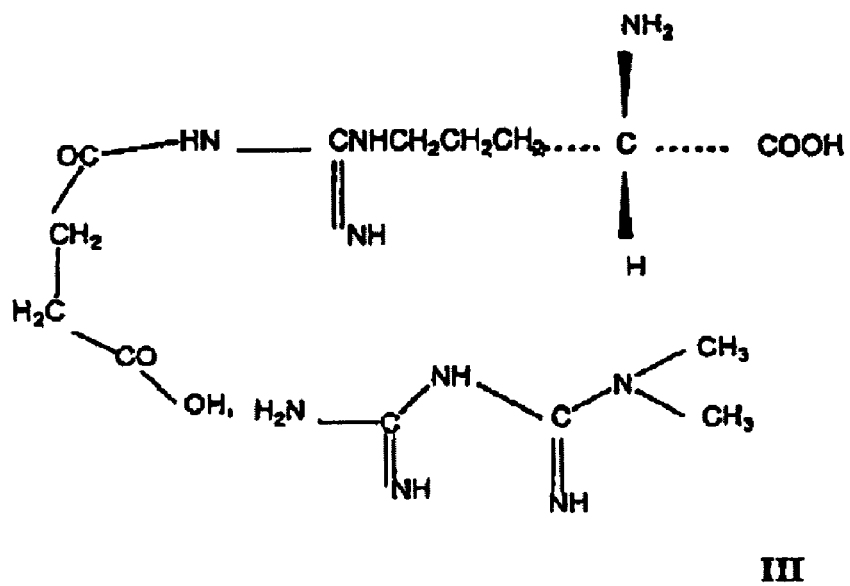

The developed formulae of the arginine, of the metformin and of the salt of the arginine hemisuccinimide with the metformin are given in FIGS. 1 to 3, respectively.

Cleavage Assay:

This assay is carried out according to the in vitro method in an intestinal juice, described above, according to the in vitro toxicity assay described. Immediate release of the metformin without modifying the arginine hemisuccinimide part is observed. A second assay is carried out on a rat hepatocyte culture, according to the method described above. A slow release of arginine over 24 hours is observed.

Toxicity:

This assay is carried out according to the in vitro toxicity assay described above. The toxic dose is observed with the metformin at $10^{-2}$ M, and it is identical for the active compound A'-V'-B', namely the salt of the arginine hemisuccinimide with the metformin.

Verification of the Pharmacological Activity of the Active Compound Obtained

The kinetic and pharmacological advantage of the active compound according to the present invention is described hereinafter, taking, by way of illustrative example, the arginine hemisuccinimide-metformin hemisuccinate, and a metformin hydrochloride/arginine hydrochloride combination:

a) a pharmacokinetic study carried out in two groups, each of 20 rats, receiving, orally, 50 mg/kg of metformin hydrochloride and 50 mg/kg of arginine hemisuccinimide-metformin hemisuccinate, respectively, made it possible to calculate the various kinetic parameters. The arginine hemisuccinimide-metformin hemisuccinate releases metformin and, in the two groups, it is the plasmatic levels of the metformin which are determined.

After administration of 50 mg/kg of metformin hydrochloride, the concentration peak is observed within 90 minutes and is found to be 3.9 µg/ml. The bioavailable fraction is 60% and the half-life is, on average, 2.5 hours.

The administration of 50 mg/kg of arginine hemisuccinimide-metformin hemisuccinate corresponds to approximately 25 mg/kg of metformin hydrochloride, i.e. to a half-dose. The concentration peak is observed at 60 minutes and it is found to be 2.9 µg/ml of metformin. The bioavailable fraction is 75% and the half-life is 2.6 hours.

These results demonstrate that the entry of the metformin (total amount and rate of transfer) is improved in the case of the arginine hemisuccinimide-metformin hemisuccinate.

From the pharmacological point of view, the anti-diabetic activity was studied on two models of rats made diabetic.

The first model consisted in treating the rate with streptozotocin (50 mg/kg, IP), this being a compound which induces an increase in glycemia, which increases from 5.5 mM to 12-14 mM in 21 days. The administration of metformin (30 mg/kg) significantly decreases this hyperglycemia, which decreases from 12.11 to 9.85 mM on average. At the same dose of 30 mg/kg (approximately two times less metformin base), the arginine hemisuccinimide-metformin hemisuccinate decreases more considerably the hyperglycemia, which decreases from 12.66 to 7.56 mM. The difference between the two treatments is significant despite the lower dose of metformin.

The second model is prepared by administering fructose at 10% in the drinking water of the rats for three weeks. An insulin resistance develops, followed by diabetes of non-insulin-resistant type. The arginine hemisuccinimide-metformin Hemisuccinate proves to be significantly more active than the metformin alone, at an equivalent dose of metformin base and the action is more rapid as shown in Table 1 below

TABLE 1

|  | Metformin 30 mg/kg/day | Arginine 30 mg/kg/day | Arginine hemisuccinimide-metformin hemisuccinate 70 mg/kg/day |
|---|---|---|---|
| Control (glycemia mM) | 6.94 ± 0.13 | 6.87 ± 0.14 | 6.84 ± 0.06 |
| 21 days fructose (glycemia mM) | 12.52 ± 0.52 | 13.24 ± 0.62 | 12.14 ± 0.28 |
| 4 days treatment (glycemia mM) | 13.41 ± 0.52 | 14.37 ± 0.20 | 10.92 ± 0.44 |

TABLE 1-continued

|  | Metformin 30 mg/kg/day | Arginine 30 mg/kg/day | Arginine hemisuccinimide-metformin hemisuccinate 70 mg/kg/day |
|---|---|---|---|
| 8 days treatment (glycemia mM) | 10.83 ± 0.64 | 12.56 ± 0.89 | 9.13 ± 0.64 |
| 12 days treatment (glycemia mM) | 9.78 ± 0.72 | 11.98 ± 0.71 | 8.43 ± 0.52 |
| 21 days treatment (glycemia mM) | 9.87 ± 0.68 | 10.73 ± 1.27 | 7.76 ± 0.78 |

The anti diabetic activity was also tested on hamsters made diabetic by the administration of fructose for three months. On this model, the arginine hemisuccinimide-metformin hemisuccinate reveals itself to be significantly more active than metformin on its own at an equal dose of 10 mg/kg/day for both products after two weeks of treatment the results illustrated in the following Table 2 are obtained:

TABLE 2

|  | Fructose 3 months | Fructose + metformin 10 mg/kg/day | Fructose + arginine hemisuccinimide-metformin hemisuccinate 10 mg/kg/day |
|---|---|---|---|
| 2 weeks treatment (glycemia mg/dl) | 143 | 112 | 93 |

Control glycemia without fructose: 91 mg/dl

A study on the cheek pouch of the hamster shows that the arginine hemisuccinimide-metformin hemisuccinate reproduces at least the effects of the two active principles on the microcirculation, namely the vasodilatory action of the arginine and the action of the metformin on vasomotion.

The invention claimed is:

1. A compound of formula III

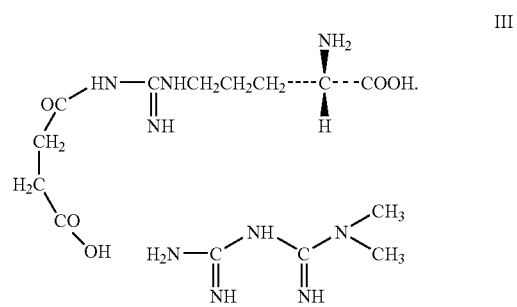

2. A method for treating diabetes in mammals, comprising administering a compound of formula III as claimed in claim 1.

3. A process for preparing an active compound of formula III as claimed in claim 1, comprising the following steps:
   (a) reaction by condensation and/or salification of succinic acid with one of arginine and metformin, and
   (b) reaction by condensation and/or salification of the product of the reaction according to (a) with the other of arginine and metformin.

* * * * *